US012560597B2

(12) United States Patent
Deissler et al.

(10) Patent No.: US 12,560,597 B2
(45) Date of Patent: Feb. 24, 2026

(54) POINT OF CARE DEVICE FOR EARLY AND RAPID DISEASE DIAGNOSIS

(71) Applicant: Case Western Reserve University, Cleveland, OH (US)

(72) Inventors: Robert Deissler, Fairview Park, OH (US); Susann Brady-Kalnay, Cleveland, OH (US); Robert Brown, Solon, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 909 days.

(21) Appl. No.: 17/839,831

(22) Filed: Jun. 14, 2022

(65) Prior Publication Data

US 2022/0308048 A1     Sep. 29, 2022

Related U.S. Application Data

(63) Continuation-in-part of application No. 17/347,892, filed on Jun. 15, 2021.
(Continued)

(51) Int. Cl.
*G01N 33/543*        (2006.01)
*G01N 21/11*        (2006.01)
(Continued)

(52) U.S. Cl.
CPC ....... *G01N 33/54326* (2013.01); *G01N 21/11* (2013.01); *G01N 21/6428* (2013.01);
(Continued)

(58) Field of Classification Search
CPC ..................... G01N 33/54326; G01N 21/6458
See application file for complete search history.

(56) References Cited

U.S. PATENT DOCUMENTS 9,575,052 B2    2/2017    Grimberg et al.
9,778,245 B2    10/2017    Grimberg et al.
(Continued)

FOREIGN PATENT DOCUMENTS

DE      102009023279.6      *   5/2009

OTHER PUBLICATIONS

Translation of DE102009023279.*
(Continued)

*Primary Examiner* — Tony Ko
(74) *Attorney, Agent, or Firm* — Tarolli, Sundheim, Covell & Tummino LLP

(57)                ABSTRACT

Early stage, rapid, low-cost detection of disease components in a biological sample is critically important. A point of care device can include a collection region and can be used to hold a sample that is combined with a fluorescent dye and a plurality of magnetic particles such that disease components in the sample are tagged with the fluorescent dye and the plurality of magnetic particles. At least one magnet can be located next to the collection region to establish a magnetic field gradient to draw the tagged disease components into the collection region from the device. A fluorescence microscope can image the small collection region based on the fluorescent dye to detect the disease components. The fluorescence microscope uses light to excite the fluorescent dye and a filter to transmit light emitted by the fluorescent dye to the fluorescence microscope, while restricting light used to excite the fluorescent dye.

19 Claims, 9 Drawing Sheets

Related U.S. Application Data

(60) Provisional application No. 63/039,317, filed on Jun. 15, 2020.

(51) Int. Cl.
   *G01N 21/64* (2006.01)
   *G01N 33/569* (2006.01)
   *G01N 33/58* (2006.01)

(52) U.S. Cl.
   CPC ... *G01N 21/6458* (2013.01); *G01N 33/56983* (2013.01); *G01N 33/582* (2013.01); *G01N 2021/6439* (2013.01)

(56)                References Cited

U.S. PATENT DOCUMENTS

| | | | |
|---|---|---|---|
| 2019/0324034 A1* | 10/2019 | Bowers | G01N 33/582 |
| 2019/0331674 A1* | 10/2019 | Connolly | G01N 27/745 |
| 2020/0008534 A1 | 1/2020 | Lovett et al. | |

OTHER PUBLICATIONS

Machine translation of 102009023279.6.*

Grimberg BT, Grimberg KO. Hemozoin detection may provide an inexpensive, sensitive, 1-minute malaria test that could revolutionize malaria screening. Expert Rev Anti Infect Ther. 2016;14(10):879-883. doi:10.1080/14787210.2016.1222900.

Hoffmann, Markus, et al. "SARS-CoV-2 cell entry depends on ACE2 and TMPRSS2 and is blocked by a clinically proven protease inhibitor." cell 181.2 (2020): 271-280.

Ibrahim IM, Abdelmalek DH, Elshahat ME, Elfiky AA. COVID-19 spike-host cell receptor GRP78 binding site prediction. J Infect. 2020;80(5):554-562. doi:10.1016/j.jinf.2020.02.026.

Lee H, Yoon TJ, Weissleder R. Ultrasensitive detection of bacteria using core-shell nanoparticles and an NMR-filter system. Angew Chem Int Ed Engl. 2009;48(31):5657-5660. doi:10.1002/anie.200901791.

Marzi A, Gramberg T, Simmons G, et al. DC-SIGN and DC-SIGNR interact with the glycoprotein of Marburg virus and the S protein of severe acute respiratory syndrome coronavirus. J Virol. 2004;78(21):12090-12095. doi:10.1128/JVI.78.21.12090-12095. 2004.

Perez, J. Manuel, et al. "Viral-induced self-assembly of magnetic nanoparticles allows the detection of viral particles in biological media." Journal of the American Chemical Society 125.34 (2003): 10192-10193.

Shao H, Min C, Issadore D, et al. Magnetic Nanoparticles and microNMR for Diagnostic Applications. Theranostics. 2012;2(1):55-65. doi:10.7150/thno.3465.

Zhou, Peng, et al. "A pneumonia outbreak associated with a new coronavirus of probable bat origin." nature 579.7798 (2020): 270-273.

* cited by examiner

500

| 502 ADD MAGNETIC PARTICLES AND FLUORESCENT DYE TO A SAMPLE |
| --- |

| ALLOW MAGNETIC PARTCLES AND DISEASE COMPONENTS IN THE SAMPLE TO INTERACT<br>504 |
| --- |

| 506 DRAW MAGNETIC DISEASE COMPONENTS INTO COLLECTION REGION |
| --- |

| 508 REMOVE NON-MAGNETIC MATERIAL OF SAMPLE |
| --- |

| 510 ROTATE MAGNET AND SAMPLE HOLDER |
| --- |

| 512 REMOVE MAGNET AND REPLACE WITH MICROSCOPE |
| --- |

| 514 IMAGE DISEASE COMPONENTS DRAWN INTO COLLECTION REGION WITH MICROSCOPE |
| --- |

FIG. 5

600
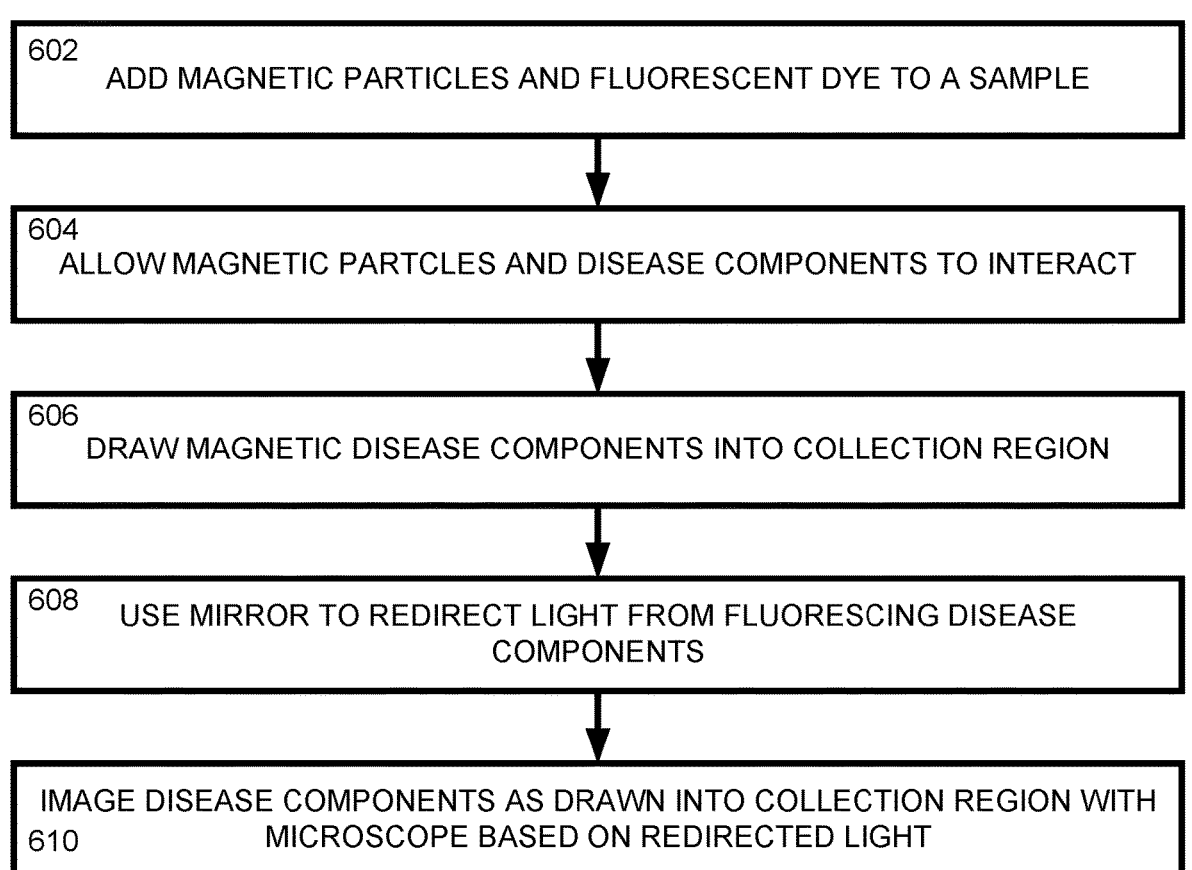
602    ADD MAGNETIC PARTICLES AND FLUORESCENT DYE TO A SAMPLE
604    ALLOW MAGNETIC PARTCLES AND DISEASE COMPONENTS TO INTERACT
606    DRAW MAGNETIC DISEASE COMPONENTS INTO COLLECTION REGION
608    USE MIRROR TO REDIRECT LIGHT FROM FLUORESCING DISEASE COMPONENTS
IMAGE DISEASE COMPONENTS AS DRAWN INTO COLLECTION REGION WITH
610    MICROSCOPE BASED ON REDIRECTED LIGHT
FIG. 6

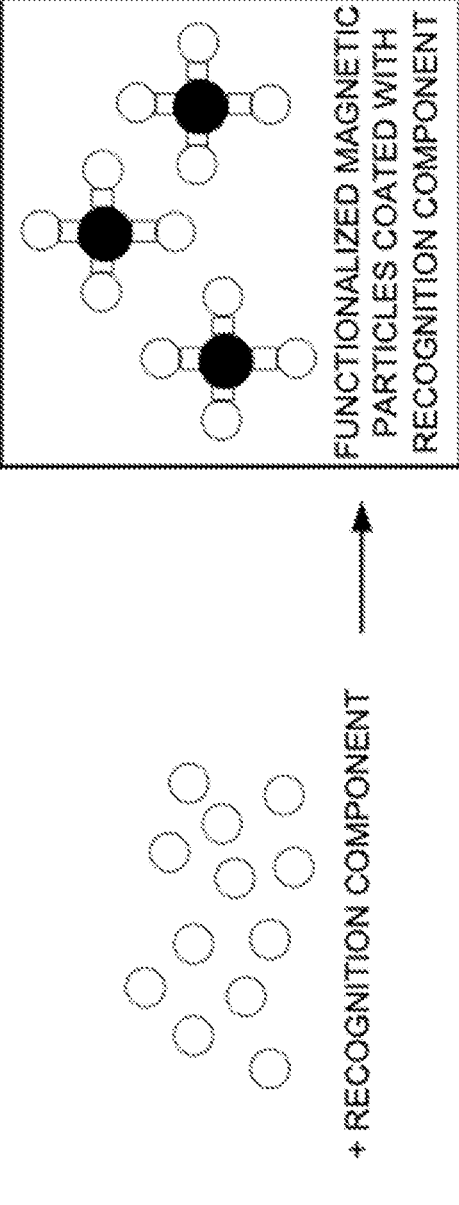
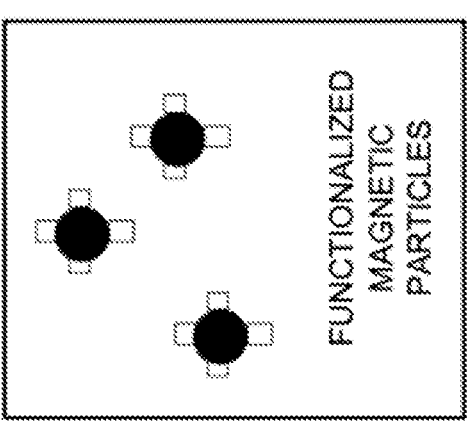
FIG. 7

POINT OF CARE DEVICE FOR EARLY AND RAPID DISEASE DIAGNOSIS

CROSS-REFERENCE TO RELATED APPLICATIONS

This application is a Continuation-in-Part of U.S. application Ser. No. 17/347,892, filed Jun. 15, 2021, entitled "POINT OF CARE DEVICE FOR EARLY AND RAPID DISEASE DIAGNOSIS", which claims the benefit of US Provisional Application No. 63/039,317, filed Jun. 15, 2020, entitled "A POINT OF CARE DEVICE FOR ANTIBODY OR VIRAL DETECTION AND CAPTURE: CAPTIV". These applications are hereby incorporated by reference in their entirety for all purposes.

TECHNICAL FIELD

This disclosure relates generally to disease diagnosis and, more specifically, to a point of care device that uses an inexpensive fluorescence microscope coupled to a computing device to detect disease components that have been pulled into a collection region of a sample holder using magnetic particles so a disease can be diagnosed in its earliest stages.

BACKGROUND

Traditionally, disease components can be detected in a patient's body some time period after initial infection, delaying the detection for a time after the original infection. During the delay, the disease components may infect the patient's body and cause or worsen an associated malady, which may make treatment more difficult. Early detection without delay would allow for more immediate treatment with a lower risk of complications or contagion. Even in instances where the disease components themselves can be detected by traditional methods a time delay is still required for the disease components to replicate and/or spread enough to be detected.

SUMMARY

Early stage, rapid, low-cost, and accurate detection of disease components is critically important in disease diagnosis and treatment. The present disclosure provides a point of care device that uses inexpensive fluorescence imaging to detect disease components that have been pulled into a collection region of a sample holder using magnetic particles. The point of care device can also be used to capture the disease components for further study and analysis, in some instances.

In accordance with an aspect of this disclosure, a system is provided that can perform critical early stage, rapid, low-cost, and accurate detection of disease components in a biological sample. A point of care device can include a collection region and can be used to hold a sample that is combined with a fluorescent dye and a plurality of magnetic particles such that disease components in the sample are tagged with the fluorescent dye and the plurality of magnetic particles. At least one magnet can be located next to the collection region to establish a magnetic field gradient to draw the tagged disease components into the collection region from the device. A fluorescence microscope can image the collection region based on the fluorescent dye to detect the disease components. The fluorescence microscope can use light to excite the fluorescent dye and a filter can transmit light emitted by the fluorescent dye to the fluorescence microscope, while restricting light used to excite the fluorescent dye.

In accordance with another aspect of this disclosure, a method is provided for detecting certain disease components in a biological sample at a critical early stage. The method includes combining a sample with a fluorescent dye and a plurality of magnetic particles in a device that includes a collection region; tagging disease components in the sample with the fluorescent dye and the plurality of magnetic particles; using at least one magnet to provide a magnetic field that draws the tagged disease components from the device into the collection region; and imaging the small collection region with a fluorescence microscope based on the fluorescent dye to detect the disease components, wherein the fluorescence microscope uses light to excite the fluorescent dye and a filter to transmit light emitted by the fluorescent dye to the fluorescence microscope, while restricting light used to excite the fluorescent dye.

BRIEF DESCRIPTION OF THE DRAWINGS

The features, objects, and advantages of the invention will become more apparent from the detailed description set forth below when taken in conjunction with the drawings, wherein:

FIGS. 5 and 6 are process flow diagram of example methods for detecting certain disease components in a biological sample using inexpensive fluorescence imaging;

FIG. 7 is an illustration of functionalized magnetic particles being coated with recognition components;

DETAILED DESCRIPTION OF THE INVENTION

Figure 1:
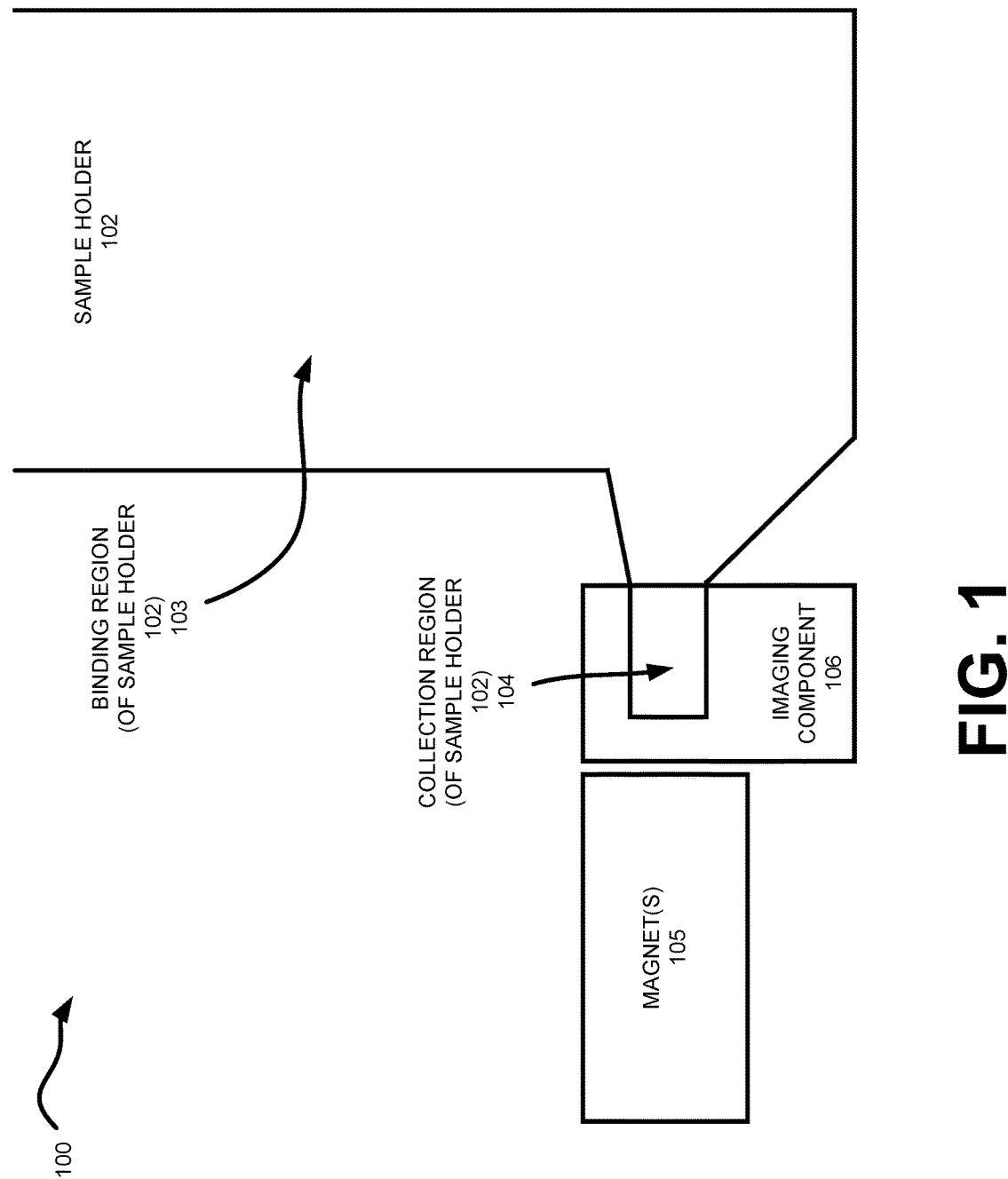
FIG. 1 is a block diagram of a system that can be used to detect certain disease components in a biological sample using inexpensive fluorescence imaging.

This disclosure relates generally to disease diagnosis based on early stage, rapid, low-cost, and accurate detection of disease components in a biological sample (magnetofluoresis). It should be understood that the biological sample, or sample, may be a solid, a fluid, or a combination of solids and fluids. With magnetofluoresis, fluorescence imaging can be performed using an inexpensive fluorescence microscope coupled to a computing device so that disease diagnosis can be performed quickly and at the point-of-care. The fluorescence microscope coupled to the portable computing device can be part of a system referred to as CAPGLO that can be used to perform magnetofluoresis to detect disease components in a sample of a biological sample. Using the CAP-GLO system, the sample can be added to a sample holder equipped with a binding region and a smaller collection region. Within the binding region, the sample can be combined with a fluorescent dye and a plurality of magnetic particles. If the sample were to include any disease components, the disease components would be tagged with the fluorescent dye and the magnetic particles. The magnetic particles can be used to pull the fluorescent, magnetic disease components into the collection region. A simple fluorescence microscope coupled to a computing device can be used to image the collection region. The fluorescence microscope or the computing device can use light to excite the fluorescent dye and a filter can transmit light emitted by the fluorescent dye to the fluorescence microscope while restricting light used to excite the fluorescent dye. The CAPGLO system has a better sensitivity of detection compared to other similar previous inexpensive detection schemes.

The disease components can be one or more antibodies, viruses, bacteria, crystals, exosomes, cells from a cancerous tissue, etc. As an example, the disease components can be cancerous cells from a biopsy. The magnetic particles can be configured to bind and/or attach to the disease components (e.g., the magnetic particles can be specifically configured to bind to a certain type of disease component). As previously noted, the detection of the disease components with the CAPGLO system can lead to earlier disease detection (e.g., before the quantity of patient antibodies detectable by current standard tests are generated) that can allow for a more immediate treatment with a lower risk of complication. The detection can be used in cases with a low-level quantity of disease components that would not traditionally be detectable. However, detection is not limited to low-level quantity detection. The diagnostic devices, systems, and methods described herein can be automated, efficient, and low cost, with the detection able to be completed within a quicker timeframe than traditional detections.

It should be noted that the disease components can be included within a sample (e.g., a fluid). The fluid can include a biological fluid originating from inside the body of a living organism and/or a non-biological fluid, like a buffer. For example, the fluid can include a concentration of the disease component but does not need to include the disease component (e.g., is being tested to see if it does include the disease component). The sample can be a fluid or can be placed within a fluid (e.g., the sample can be cells or tissue from a biopsy). In some instances, at least a portion of the sample and/or the fluid can undergo processing, such as digestion and/or dilution. In some instances, the sample can include cells or tissue from a biopsy.

It should be understood that a biological fluid (also referred to as a "biofluid") can be any type of fluid or tissue (which has been placed within a fluid that may or may not originate from the body) originating from an organism (e.g., bacteria, virus, fungi, plant, human or animal) that is known to potentially house the disease component. Different disease components can be housed in different biofluids. More than one type of disease component can be housed in the same biofluid also. Biofluids can be excreted (such as sputum, nasal excretions, urine or sweat), secreted (such as breast milk), obtained with a needle (such as synovial fluid, blood, or cerebrospinal fluid), or developed as a result of a pathological process (such as blister fluid or cyst fluid). Cell culture media can also be a type of biofluid. As used herein, a "sample" can be a portion of biofluid being tested to see if a certain disease component exists therein.

An example configuration a system 100 that can be used to detect certain disease components in a sample (e.g., a fluid, a biological fluid) using magnetofluoresis as shown in FIG. 1. In some instances, the system 100 can also be used to capture the disease particles for further analysis. At least a portion of the system 100 can be a part of CAPGLO, a point of care device that can be used in a doctor's office, at a patient's home, in an emergency room, at a pharmacy, etc. However, it should be understood that CAPGLO can also be used in a laboratory setting.

The system 100 can include a device (referred to a sample holder 102) that can be configured to hold an amount of a sample (e.g., a sample and an accompanying fluid, such as a biofluid) that may or may not include a disease component. The biofluid can be any type of fluid or tissue as described above that is known to potentially house the disease component (e.g., although the particular biofluid being tested may or may not include the disease component the disease component is known to be found in the same biofluid in other similar living organisms). Different disease components can be housed in different biofluids. It should be noted that one or more types of disease components can be housed in the same biofluid. The sample holder 102 can be made of one or more transparent or translucent materials, such as one or more plastics, glass, or a combination of one or more plastic and glass. As an example, at least a portion of the sample holder 102 can be a cuvette. It should be noted that although the sample holder 102 is illustrated as having one or more rectangular/cubed shapes, this is for ease of illustration; the sample holder 102 can have one or more rounded edges or be other shapes (e.g., elliptical, triangular, polygonal, etc.).

The sample holder 102 can include a binding region 103 and a collection region 104 (also referred to as a "pocket"). The collection region 104 can have a dimension (e.g., length, height, width, depth, etc.) smaller than the sample holder 102 (e.g., an entire side of the binding region 103). The binding region 103 can be configured to hold the sample (which may or may not include a disease component), while the collection region 104 can be configured to at least collect and in some instances capture a disease component therein (when the disease component is in the sample). As shown in FIG. 1, the collection region 104 can be located along a vertical side of the binding region 103. It should be noted that although collection region 104 is only shown against a vertical side of the binding region 103, the collection region 104 may be along at least a portion of a bottom of the binding region 103, or against any one or more sides of binding region 103. In some instances, the binding region 103 can have a larger interior volume than the volume of the collection region 104. The binding region 103 and the collection region 104 can be contiguous parts of a single sample holder 102 that shrinks down, changes shape, or tapers from the binding region 103 to the collection region 104.

Magnetic particles (that are functionalized and may include specifically designed reception components for the disease component) and one or more fluorescence markers (e.g., fluorescent dyes) can be added to the sample in the sample holder 102 to facilitate the detection of at least one disease component. The magnetic particles can include or be made of any magnetic material that is natural and/or man-made. Each of the magnetic particles can be of any 2-dimensional (e.g., negligible depth) or 3-dimensional shape having a size less than 100 microns (the size can be a distance from one side of the particle to another in a line, like a diameter if the microparticle are of a circular shape). For example, each magnetic particle can have a size less than 50 microns, less than 25 microns, less than 1 micron, etc. As another example, each magnetic particle can have a size greater than 10 nanometers, but less than 50 microns. The magnetic particles, in some instances, can be functionalized to bind to, attach to, or otherwise complex with a binding component for the disease component (which can be specific for binding to a certain disease component, like antibodies, peptides, proteins, nucleic acids, etc.) or the disease component itself, such that the magnetic particles can be put into a sample that may include the disease component and then bind or otherwise form complexes with any of the disease component in the sample (e.g., the certain disease component and may include a fluid). In some instances, the magnetic particles can be functionalized to bind directly or can be functionalized with a linker molecule attached to the magnetic particles' surfaces in order to modify the physical and/or chemical properties so that one or more recognition components can bind to and/or coat the magnetic particle. The linker molecule can be any molecule that is functionally attached (e.g., covalently linked) to a magnetic particle that creates an adhesion point for a recognition component. The recognition component can be a viral protein, an envelope associated cellular protein, a proteinase, a coat protein, an envelope protein, a spike protein, an antibody, an antibody fragment, a peptide, a nucleic acid, or the like.

As one example, a functionalized magnetic particle can be a magnetic particle that has had a linker molecule attached to the magnetic particle's surface in order to modify the physical and/or chemical properties of the magnetic particle so that one or more recognition components can bind to and/or coat the magnetic particle. The linker molecule can be any molecule that is functionally attached (e.g., covalently linked) to a magnetic particle and creates an adhesion point for a recognition component. For example, the linker molecule may be any cellular based protein. The recognition component can be a protein, such as viral protein, an envelope associated cellular protein, a proteinase, a coat protein, an envelope protein, a spike protein, an antibody, an antibody fragment, a peptide, a nucleic acid, or the like. As an example, the recognition component can be an Fc chimera protein such as ACE-2-Fc, TMPRSS2-Fc, GRP-78-Fc, DC-SIGN-Fc, or DC-SIGNR-Fc. As another example, the recognition component can be a native and/or a recombinant protein, like one of M, E, S, N, HE, 3, 6, 7, 8, 9, 10, NSP and ORF proteins. In fact, the protein can be a viral associated protein derived from infected cells. As a further example, the recognition component can be a nucleic acid, including at least a portion of RNA or DNA. As another example, the magnetic particles can be functionalized with the recognition component without requiring a linker molecule. As a further example, recognition components can be previously bound to disease components and then the recognition component can be attached to the functionalized magnetic particles. It should be noted that the linker molecule and/or the recognition component may be unnecessary to functionalize the magnetic particles, which may be functionalized in a different way.

More specifically, the magnetic particles can be added to the binding region 103 of the sample holder 102 so that one or more of the magnetic particles can attach to the disease components. In some instances, more than one magnetic particle can attach to a single disease component. Certain magnetic particles (or attachments to the magnetic particles) can attach to more than one disease component, in some instances, allowing the creation of clusters of disease components. Depending on the size of the disease component, multiple magnetic particles can attach to a disease component (forming a coating or clusters of magnetic particles) or a magnetic particle can attach to multiple disease components.

A fluorescent dye (also referred to as a fluorescent tracker) can also be added to the disease components (if the disease components are within the sample). Fluorescent molecules of the fluorescent dye/tracker may bind to the disease components in the sample (this may occur by adding the fluorescence tracker before the sample is placed in the sample holder 102 or after the sample is placed in the sample holder 102 at any point before the detection). Additionally, or alternatively, a different fluorescent dye/tracker (e.g., a different color, fluoresces at a different wavelength of light, etc.) can be added to the magnetic particles. In one example, the disease components can be tagged with a fluorescent molecule (e.g., FITC) or a fluorescent dye (e.g., lipophilic dye). For example, FITC can fluoresce green when exposed to blue light. Regardless of the specific fluorescent molecule, the fluorescent molecule can fluoresce at a wavelength that is longer than the wavelength chosen for the initial light source. The fluorescent dye can be uptaken at least by any disease components so that the disease components become fluorescence emitters when excited. In some instances, the fluorescent dye can be embodied on or with the magnetic particles. In other instances, all elements within the sample can be tagged with the fluorescent dye, but only some include the magnetic particles, so only some are able to be detected (e.g., are collected in collection region 104). It should be noted that when the disease components are cells from a biopsy, the disease component can be made fluorescent by using a lipophilic dye or fluorescent fusion protein.

One or more magnets 105 can be positioned to establish a magnetic field gradient that can draw the magnetic disease components into the collection region 104. It should be noted that the magnet(s) 105 in FIG. 1 can be positioned on any side of the sample holder 102. For example, the one or more magnets 105 can include a single magnet that is polarized to be north/south, with the north side closer to the collection region 104 and the south side away from the collection region 104. The one or more magnets can be positioned on an opposite side of the collection region 104 from where the collection region and the binding region 103 are connected (e.g., are in fluid communication). It will be understood that different configurations of the one or more magnets 105 are possible as long as the magnet(s) establish a magnetic field gradient that can draw the disease components with magnetic particles attached thereto into the collection region 104. The magnets 105 can be moveable or able to be shielded, in some instances.

The one or more magnets 105 can include at least one simple, inexpensive lab magnet. However, the one or more magnets 105 can also include a permanent magnet. Generally, permanent magnets can produce a high magnetic field with a low mass. Additionally, a permanent magnet is generally stable against demagnetizing influences. For example, this stability may be due to the internal structure of the magnet. The permanent magnet can be made from a material that is magnetized and creates its own persistent magnetic field. The permanent magnet can be made of a hard ferromagnetic material, such as alcino or ferrite. However, the permanent magnet can also be made of a rare earth material, such as samarium, neodymium, or respective alloys.

As another example, the one or more magnets 105 can include an electromagnet. An electromagnet can be made from a coil of a wire that acts as a magnet when an electric current passes through the coil, but stops being a magnet when the current stops. The coil can be wrapped around a core of a soft ferromagnetic material, such as steel, which greatly enhances the magnetic field produced by the coil. For example, the magnetic field can be between about 0.01 T and about 100 T. As another example, the magnetic field can be between about 0.1 T and 10 T. As a further example, the magnetic field can be between 0.1 T and 2 T.

The magnetic field gradient created by the one or more magnets 105 can pull the magnetic particles (which may be functionalized or functionalized and coated with recognition component) attached to the disease components into the collection region 104. The unbound magnetic particles are affected by the magnetic field gradient, but not to the same extent as the magnetic particles bound to disease component (e.g., single magnetic particles that are not bound to a disease component, and are therefore smaller, also move under the magnetic field gradient, but to a lesser degree than those bound to the disease component, which are therefore larger in size). Larger magnetic particles are more affected by the magnetic field gradient than smaller magnetic particles, for example, at a chosen magnetic field gradient strength, 10 nm individual unbound magnetic particles would not be pulled into the collection region 104. To keep the majority of unbound magnetic particles out of the collection region 104, distinct field gradient strengths may be utilized for different size particles. Magnetic particles that are bound to one or more disease components can be pulled towards the collection region 104 at a greater speed or acceleration than the individual particles. Simply, it should be noted that magnetic material can be drawn into the collection region 104, but only the disease component(s) will glow. In other words, only magnetic material moves under the magnetic field gradient, but only the composite magnetic particle-disease component will fluoresce.

An imaging component 106 can provide the magneto-fluoresis by detecting the disease components within the collection region 104 (or as they are being drawn into the collection region 104). The imaging component 106 can include a light source and a detector. The detector can include one or more of: a filter or multiple filters, a digital microscope and/or photodetector, and a computing device (e.g., a smart phone or laptop that can be attached to the digital microscope). As an example, the imaging component 106 can include a microscope linked to a computing device and may include one or more of a light source, a mirror, a filter, and the like. As an example, the microscope can be a fluorescence microscope that may be an attachment to a mobile phone. The fluorescence microscope can image the collection region 104 based on the fluorescent dye to detect the disease components. The fluorescence microscope can use light to excite the fluorescent dye and a filter can transmit light emitted by the fluorescent dye to the fluorescence microscope, while restricting light used to excite the fluorescent dye. The fluorescence microscope can also detect the light allowed to pass by the filter.

For example, the computing device of the detector of the imaging component 106 can regulate delivery of light, record data (e.g., sampling the detector), analyze data, determine appropriate configurations of the one or more magnets 105 during the detection process, or the like. The computing device of the detector can include a memory storing instructions (that may be pre-programmed) and a processor configured to access the memory and execute the instructions. The computing device of the detector can, in some instances, be connected to a display to visualize an image of the collection region 104, results of data analysis, one or more calculations of the analysis, or the like. As an example, the computing device can communicate with other devices via a communication protocol like BLUETOOTH, BLUETOOTH low energy, WIFI, etc.

In some instances, the system 100 can capture disease components for further analysis. In some examples, the disease components can be isolated from a sample and captured for further study. In other examples, the disease components can be either detected then captured or captured then detected. For example, the detection may be confirmed by the capture of disease components.

Advantageously, the system 100 permits capture of at least the disease component for follow up studies. The collection region 104 can be used to facilitate the capture of disease components for further testing and analysis. The one or more magnets 105 can move or be shielded to facilitate the capture. In one example, the clusters can be captured and removed from the collection region 104. In another example, the clusters captured in the collection region 104 can be washed to remove the functionalized magnetic particles. The isolated disease components can then be collected, for example with a micro-pipette, for further testing and/or follow-up studies, allowing for a patient-specific approach to isolate and analyze the molecular and cellular properties of an individual patient's disease component.

Figure 2:
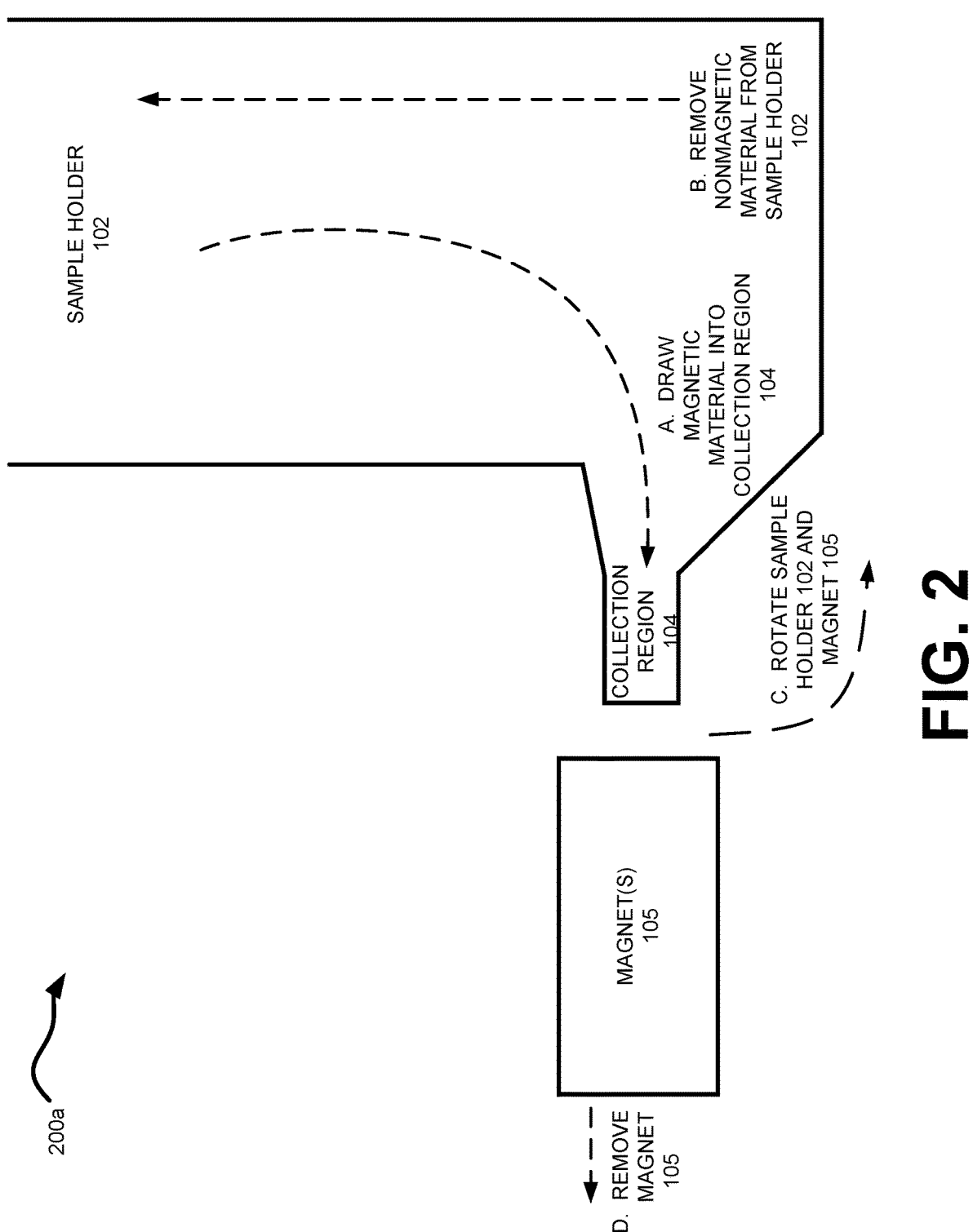
FIGS. 2 and 3, taken together, are block diagrams showing an example operation of the system of FIG. 1 detecting certain disease components in a biological sample using inexpensive fluorescence imaging.
Figure 3:
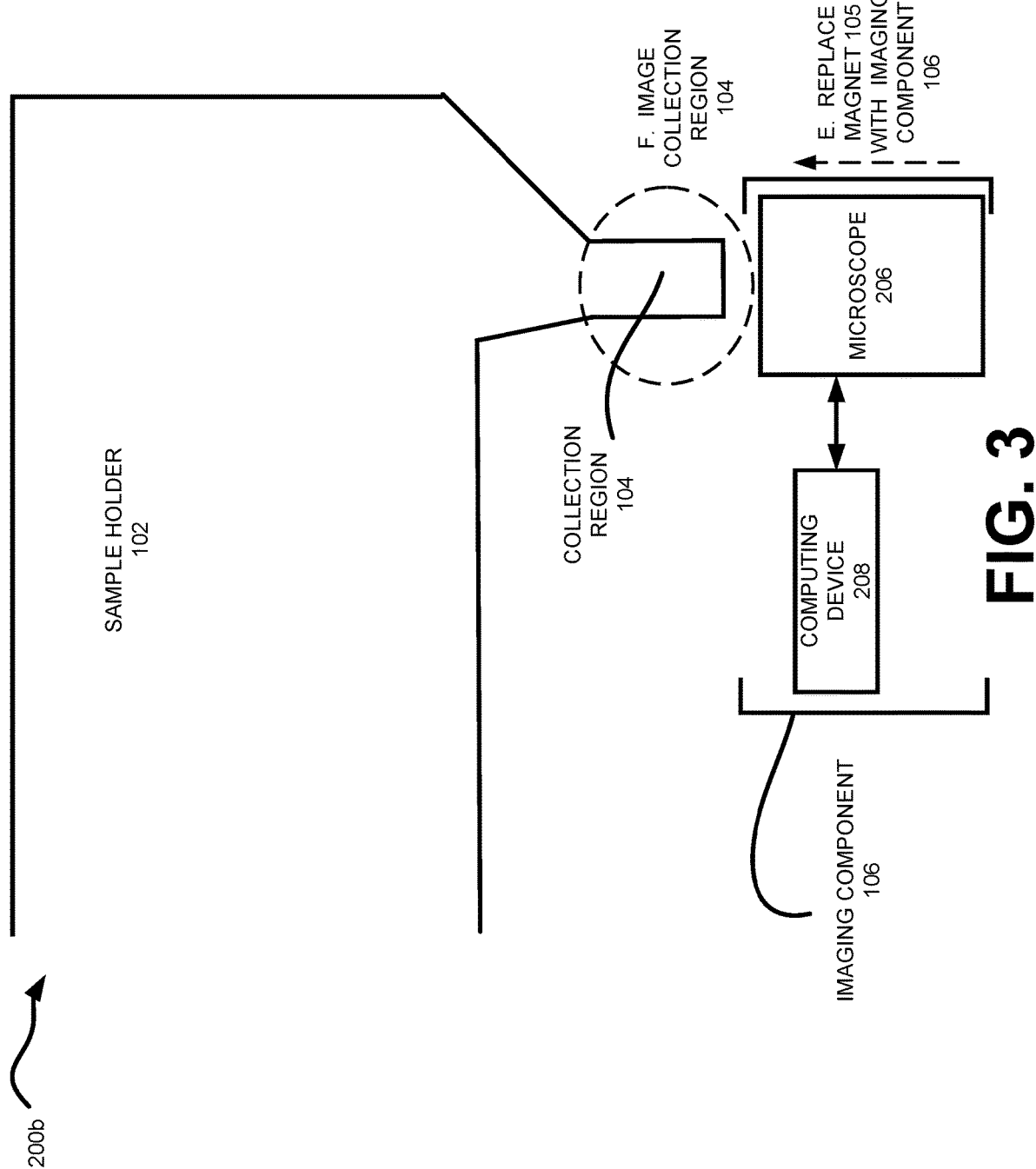
Figure 4:
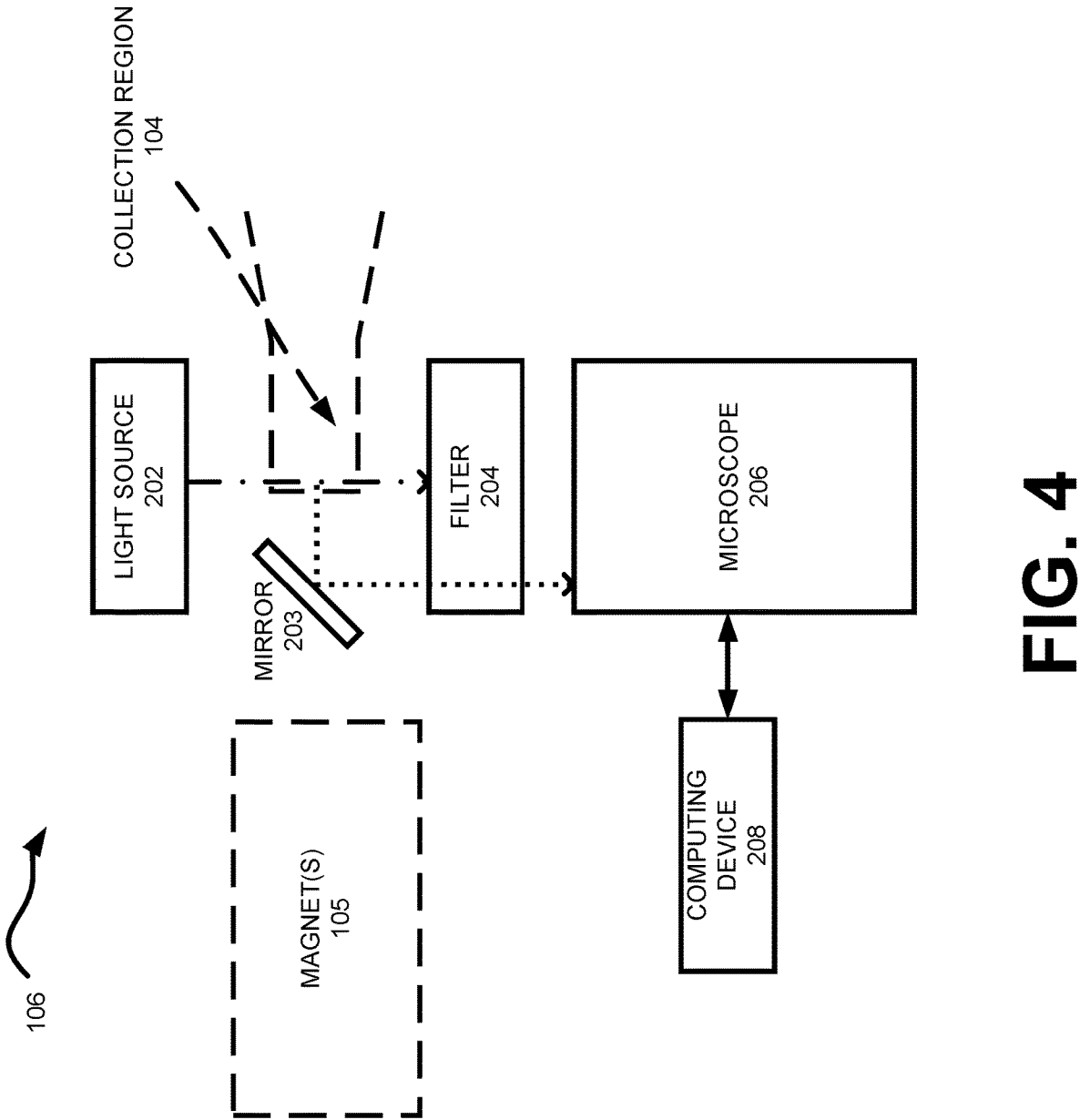
FIG. 4 is a block diagram of another example operation of the system of FIG. 1 detecting certain disease components in a biological sample using inexpensive fluorescence imaging.

Different example uses of the imaging component 106 are shown in FIGS. 2-3 (a standard detection of disease particles in the collection region 104) and FIG. 4 (detection as disease components enter the collection region 104). These example uses are not meant to be exclusive.

As noted, FIGS. 2-3 show an example of detection of disease particles in the collection region 104 after the disease particles have been pulled into the collection region. It should be understood that one or more of the actions shown and described in FIGS. 2-3 can be undertaken manually and/or undertaken by a software-controlled process (e.g., implemented by a controller or other computing device with a processer in communication one or more components capable of undertaking the actions described).

In FIG. 2, the system 200a is shown with steps A-D. Magnetic particles and a fluorescent dye are added to the sample (in sample holder 102). It should be noted that the sample either includes disease components or does not include disease components. If the sample includes disease components, at least some of the magnetic particles can attach to the disease components (magnetic particles and/disease components with attached magnetic particles referred to as magnetic material in step A). If the sample does not include disease components, then the magnetic particles attach to nothing. As shown in step A, the magnetic material can be drawn into the collection region 104 using one or more magnets 105, speed and size of magnetic material drawn in can depend on the magnetic field strength utilized. After the magnetic material is drawn into the collection region, according to step B, any non-magnetic material within the sample holder 102 can be removed leaving only the disease components and any magnetic particles attached to the disease components (some magnetic particles that are not attached to the disease components may also be in the collection region 104). The non-magnetic material can include red blood cells and other non-disease components of blood or other bodily fluids. In some instances, magnetic particles not attached to disease components, and not in the collection region 104, can also be removed with the non-magnetic material. The removal of the non-magnetic material can be done by adding PBS buffer (or any other fluid) to the sample holder 102 and then removing the PBS buffer (or other fluid) using a micropipette.

Then, according to step C, after the non-magnetic material is removed, the sample holder 102 and magnet(s) 105 can be rotated 90 degrees about a horizontal axis (shown rotated in FIG. 3) and according to step D, the magnet(s) 105 can be removed when the rotation is complete with the magnetic material being held in place in the collection region 104 by gravity. However, although rotation is illustrated, it should be noted that the rotation is optional and that the system 200a, 200b can work without rotation and the magnet(s) can be removed and replaced with a different component that holds the disease components in place or can stay in place to hold the disease components in place. As shown in FIG. 3, the system 200b is shown with steps E and F (continuing from step D of FIG. 2). According to step E, the magnet(s) 105 can be replaced with the imaging component 106. The imaging component 106 includes at least a microscope 206 coupled to a computing device 208 (e.g., a smartphone with a portable fluorescence microscope adaptation). It should be noted that the imaging component 106 can also include, as part of the microscope 206 or as separate components, one or more light sources, one or more filters, one or more mirrors, or the like, even though these additional components are not illustrated in FIG. 3. According to step E, the collection region 104 can be imaged using the imaging component 106. The imaging can include adding light to cause the fluorescent dye to fluoresce, filtering the light used to create the fluorescence from the light indicating fluorescence, and taking a picture/video (referred to as images) of the light indicating the fluorescence. The images taken can be used to detect any disease components within the collection region 104. If no disease components were in the sample, then the image will contain little or no fluorescence.

As noted, the imaging component 106 can include a smartphone with a portable fluorescence microscope adaptation to image the fluorescing cells. However, similar results can be obtained using an inexpensive digital microscope, a blue LED to excite the fluorescent dye, and a green filter to transmit only the green color emitted by the dye. The field of view for the microscope 206 can be chosen to be the same size as the end of the collection region 104 where the trapped magnetic material resides. As an example, if the diagonal of the square end of the collection region 104 is 2 mm, the field of view for the microscope 206 should be chosen to be the same, so that all captured disease components may be seen on a display of the computing device 208. In this example, all trapped disease components (with magnetic particles attached) will be in the field of view of the microscope 206, so that no disease components are missed, allowing for the detection of a small number of disease components (e.g., for a small number of disease components per mL) present in a given sample (e.g., just after infection with a disease). The small number depends on the sensitivity of the size of the sample holder 102—such that in a 1 mL sample holder 102, the small number of particles can be several disease components per milliliter with the sensitivity increasing as the size of the sample holder increases. In some instances, it may be possible to replace the microscope 206 with a photodiode to detect (e.g., by the computing device 208) the intensity of light emitted by the fluorescent dye, where the detected intensity can give an indication of the degree of infection. However, fluorescence microscopy is preferred because having an actual image of the fluorescing disease components would instill confidence in the existence of an infection.

In addition to imaging the fluorescing disease components, the computing device 208 can count the number of fluorescing disease components and determine the number of the disease component per milliliter, depending on a known volume of the sample in the sample holder 102. For example, if 1 mL of blood is drawn from a patient and inserted into a 1 mL sample holder 102, and if 5 fluorescing disease components are counted, the degree of infection would be 5 disease components/mL of blood. If 5 mL of blood are drawn from a different patient and inserted into a 5 mL sample holder 102, and if 5 fluorescing cells are counted, the degree of infection would be 1 disease component/mL of blood.

FIG. 4 shows changes (additional components) to the imaging component 106 necessary to detect disease components as the disease components are drawn into the collection region 104 (components of the system 100 that are not part of the imaging component 106, the collection region 104 and the magnet(s) 105, are illustrated in dashed lines). As shown in FIG. 4, the magnet(s) 105 can remain in place during the imaging in this instance. A light source 202 can provide a light beam (long-dashed and dotted line) through a portion of the collection region 104. Any disease components tagged with fluorescent dye can be excited by the light (e.g., the fluorescent dye fluoresces in response to the light). A mirror 203 (e.g., a small mirror) can be used to redirect light emitted by the fluorescing disease component(s) (the redirected light shown as a small-dashed line) toward the microscope 206. Before the light (the redirected light from the fluorescing disease component(s) and the light beam from the light source 202) reaches the microscope 206, the light can pass through a filter 204. The filter can prevent at least a majority of the light from the light source 202 from passing through the filter but can allow the redirected light from the fluorescing disease component(s) to pass. For example, the filter 204 can filter out certain wavelengths of light while allowing other wavelengths of light to pass through. The microscope 206 and the computing device 208 can receive and process the filtered light (e.g., primarily the light redirected from the fluorescing disease components(s)). The computing device 208 can determine (quantitatively and/or qualitatively) the number of disease components entering the collection region 104.

In view of the foregoing structural and functional features, example methods for magnetofluoresis will be better appreciated with reference to FIGS. 5 and 6. While, for purposes of simplicity of explanation, the methods of FIGS. 5 and 6 are shown and described as executing serially, it is to be understood and appreciated that the present invention is not limited by the illustrated order, as some actions could, in other examples, occur in different orders from that shown and described herein or could occur concurrently. It will be appreciated that some or all acts of methods 500 and 600 can be implemented as machine-readable instructions on a non-transitory computer readable medium.

FIG. 5 illustrates an example standard method 500 for detecting disease components in a sample (e.g., within a biological fluid). At 502, magnetic particles and fluorescent dye can be added to a sample (e.g., in a sample holder with a collection region). It should be noted that the sample either includes disease components or does not include disease components. The disease components and/or the magnetic particles can interact with the fluorescent dye as described in detail above. At 504, the magnetic particles and the disease components can be allowed to interact to form magnetic disease components (if there are disease components in the sample). At 506, the magnetic disease components can be drawn into a collection region using at least one magnet positioned near the collection region. If there are no disease components in the sample, then only the magnetic particles can be drawn into the collection region. At 508, the non-magnetic material of the sample can be removed from the sample holder (leaving only the magnetic disease components and/or magnetic particles). The non-magnetic material can include red blood cells and other non-disease components of blood or other bodily fluids. At 510, the at least one magnet and the sample holder can be rotated (e.g., 90 degrees from a horizontal axis). At 512, the at least one magnet can be removed and replaced with a microscope. The at least one magnet is no longer necessary because the magnetic disease components can be held in place in the collection region by gravity following the rotation. At 514, the collection region can be imaged with the microscope. The microscope can be coupled to a computing device (e.g., a smartphone with a portable fluorescence microscope adaptation). It should be noted that the microscope can also include one or more light sources, one or more filters, one or more mirrors, or the like. The field of view for the microscope can be chosen to be the same size as the end of the collection region where the trapped magnetic disease components reside. Additionally, the disease components can be captured for further analysis using the collection region.

FIG. 6 illustrates another example method 600 for detecting disease components in a sample as they are drawn into a collection region. At 602, magnetic particles and a fluorescent dye are added to a sample (e.g., in a sample holder with a collection region). It should be noted that the sample either includes disease components or does not include disease components. The disease components and/or the magnetic particles can interact with the fluorescent dye (as described in detail above). At 604, the magnetic particles and the disease components can be allowed to interact. At 606, magnetic disease components can be drawn into the collection region. A light source can provide a light beam through the collection region. Any disease components tagged with fluorescent dye can be excited by the light beam. At 608, a mirror (e.g., a small mirror) can be used to redirect the light from fluorescing disease components that are excited by the light beam. At 610, the disease components can be imaged as they are drawn into the collection region with the microscope. Before the light (the redirected light from the fluorescing disease component(s) and the light beam from the light source) reaches the microscope, the light must pass through a filter. The filter can prevent at least a majority of the light from the light source from passing through the filter but can allow the redirected light from the fluorescing disease components to pass. The magnet(s) can remain in place throughout the method 600, including during the imaging. Additionally, the disease components can be captured for further analysis using the collection region.

EXAMPLE

The CAPGLO functionality described above can be used with the CAPTIV system for early detection of a number of different diseases, such as COVID-19. COVID-19 is the disease caused by the pathogenic coronavirus SARS-CoV-2. Early detection of viruses and/or anti-viral antibodies is vital with pathogens, like SARS-CoV-2. Two types of tests are available for COVID-19, a viral test (e.g., a nucleic acid amplification test or an antigen test) and an antibody test (e.g., a serology test). A viral test can determine whether a patient is currently infected. An antibody test can determine whether a patient has had a past infection. However, detecting the SARS-CoV-2 virus or a body's antibody response to the SARS-CoV-2 virus using these new diagnostic approaches may require days or weeks beyond the first exposure. When a COVID-19 infection can be detected in its earliest stages, fewer people will be exposed to the SARS-CoV-2 virus, thereby slowing the spread of COVID-19.

At its core, the CAPTIV system can perform a test for the coronavirus (specifically the SARS-CoV-2 virus or antibody). Using the CAPTIV system, the virus or antibody can be detected in a biofluid sample (including a sample taken from the patient, which may need to be diluted with a buffer like PBS or ultrafiltered water or put into a fluid) and captured for further study. It should be understood that while COVID-19 is one example disease and SARS-CoV-2 is one example virus, the CAPTIV system with CAPGLO functionality represents a platform that can be adapted to detect and capture any disease component as long as the magnetic particles specifically attach to the disease component.

Additionally, the CAPTIV system that can be provided with CAPGLO functionality can capture the SARS-CoV-2 virus or associated antibodies for further analysis. Advantageously, the disease particles can be captured while coupled to the recognition component, or after release from the recognition component, so that the disease component can be further studied in a "patient-derived" approach that allows analysis of the nuances or specificity of the disease component (e.g., as part of a cluster) in a biofluid sample of a particular patient. The CAPTIV system that can be provided with CAPGLO functionality can serve a great need by determining the presence of an infection in a patient or an antibody response of the patient's immune system to help to control the spread of COVID-19 and overcomes issues with the sensitivity of detection due to many obstacles, including the low amount of SARS-CoV-2 virus or associated antibodies in the amount of biofluid tested (which can lead to false negatives) or the long time after infection/exposure for SARS-CoV-2 virus or associated antibodies to reach a detectable level (when unknowing community spread can occur).

Using the CAPTIV system, a biofluid sample to be tested (e.g., the sample can hold a portion of a patient's biofluid) can be added to a sample holder (e.g., similar to the sample holder of FIG. 1). Functionalized magnetic particles can also be added to the biofluid sample (e.g., in the binding region 103 of sample holder 102 of FIG. 1). The magnetic particles that can be functionalized and, in some instances, coated with recognition components to facilitate detection of the disease components in a biological fluid (shown in FIG. 7). It should be noted that the functionalized magnetic particles may also be referred to as magnetic beads.

Before being added to the biofluid sample, the magnetic particles can be functionalized and then coated with a recognition component (e.g., viral receptors/ligands specific for SARS-CoV-2 or viral proteins specific for antibodies). The viral receptors/ligands specific for SARS-CoV-2 can include receptor Fc proteins, including ACE-2-Fc TMPRSS2-Fc, GRP-78-Fc DC-SIGN-Fc or DC-SIGNR-Fc. The viral proteins specific for antibodies can include native or recombinant proteinases, coat proteins, envelope proteins, or spike proteins. Both native and recombinant proteins, like M, E, S, N, HE, 3, 6, 7, 8, 9, 10, NSP and ORF proteins, viral associated proteins derived from infected cells, and RNA/DNA nucleic acid from the virus). The functionalized magnetic particles coated with recognition components can facilitate an amplification effect through clustering of attached magnetic particles. As used herein, a "cluster" can include a plurality of magnetic particles, a plurality of recognition components, and one or more disease components bound together. A cluster can be formed when at least one recognition component, attached to a functionalized magnetic particle, binds to a disease component. Due to their larger size than a single disease component alone, clusters can allow for disease components to be captured and detected at smaller numbers than traditional detection schemes using a magnetic gradient.

Figures 8, 9:
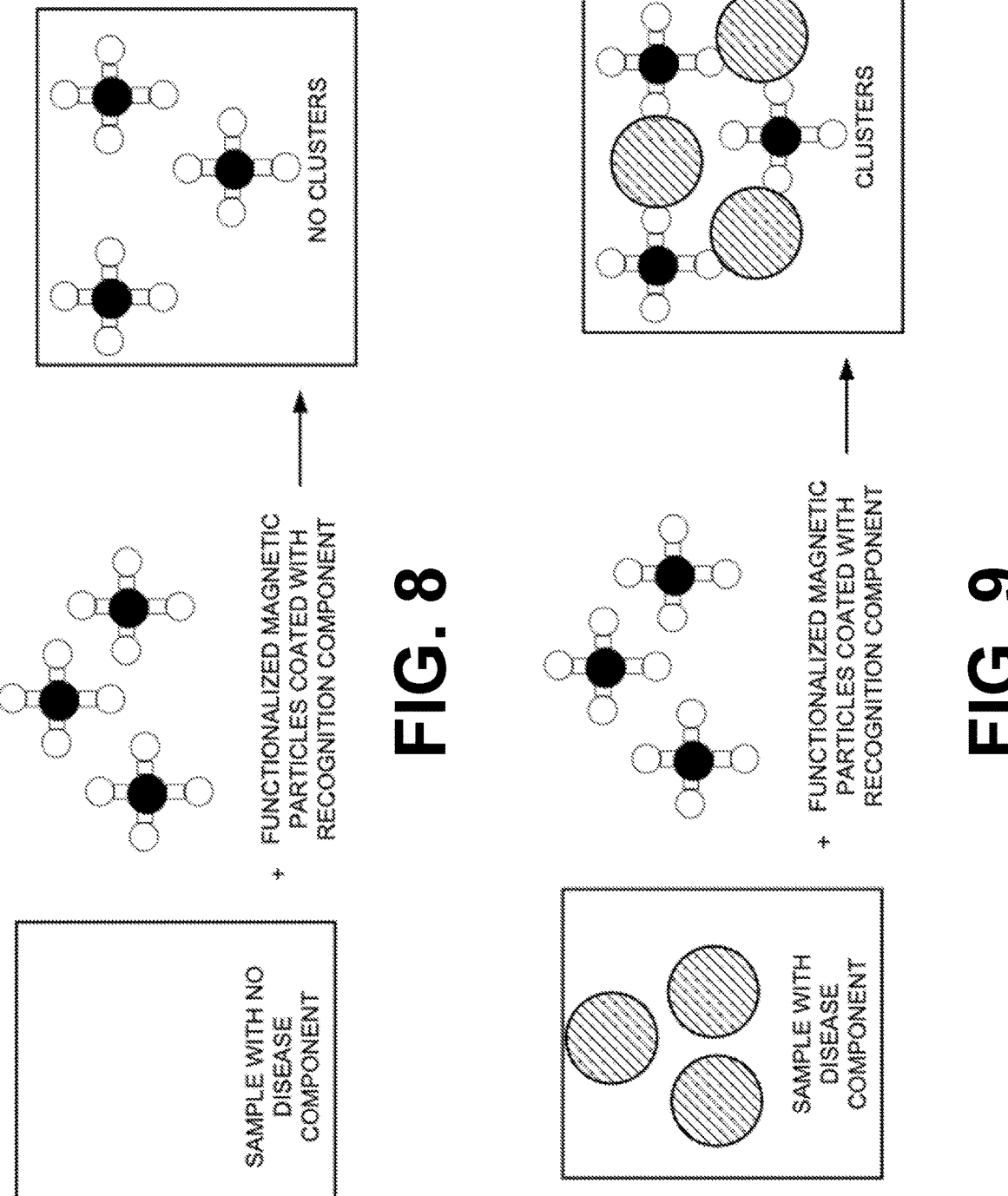
FIGS. 8 and 9 are illustrations of what happens when functionalized magnetic particles coated with recognition components are placed in a sample without a disease component (FIG. 8) and with a fluorescing disease component (FIG. 9)

As shown in FIG. 7, before the functionalized magnetic particles are added to the sample holder, the functionalized magnetic particles can be coated with recognition component. In some instances, the recognition component can be selected based on the target disease component (in this case, the SARS-CoV-2 virus or associated antibodies). In other instances, the recognition component can be selected generally to detect a variety of different disease components. The disease component can be an antibody, a virus, a bacterium, a fungus, a crystal, an exosome, a cell from a cancerous tissue, etc. If the sample contains none of the targeted disease component, then the functionalized magnetic particles coated with recognition components will not attach to anything. As shown in FIG. 8 when no disease component is within the sample, no clusters are formed. However, as shown in FIG. 9, when disease components are present within the sample, clusters are formed. Clusters can be as small as a single disease component with at least one functionalized magnetic particle attached via a recognition component. Preferably the smallest clusters can include a single disease component with at least two functionalized magnetic particles each attached to the disease component via a recognition component. Clusters can also be of a larger size, including a plurality of disease components connected with each other via bindings to a plurality of recognition components coating a plurality of functionalized magnetic particles, such as shown in FIG. 9 (the disease components are stained with a fluorescence dye). It should be noted that magnetic material can be drawn into the collection region 104, but only the disease component(s) will glow (or fluoresce). In other words, only magnetic material moves under the magnetic field gradient, but only the composite magnetic particle-disease component will fluoresce.

Figures 10, 11:
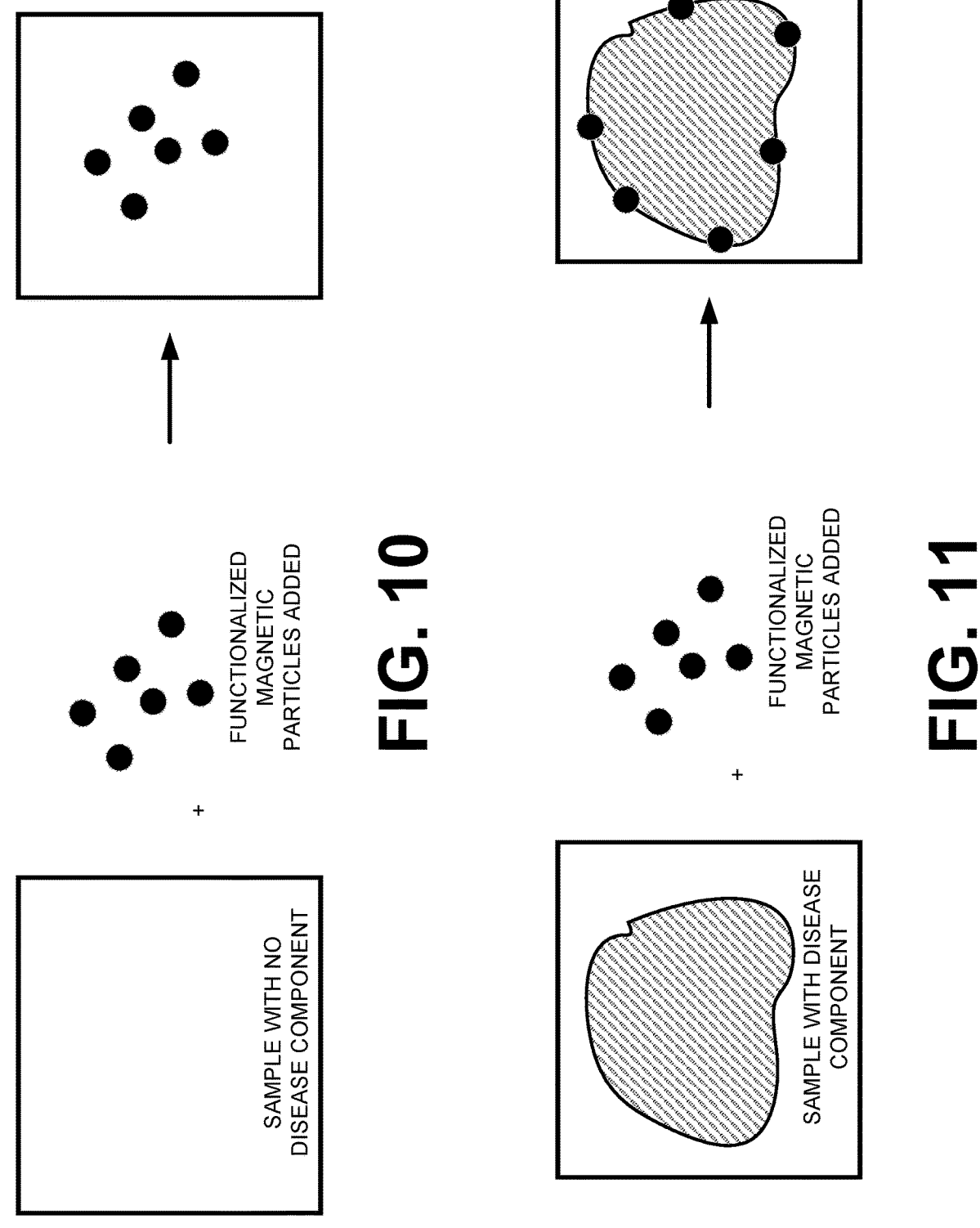
FIGS. 10 and 11 are illustrations of what happens when functionalized magnetic particles are placed in a sample without a disease component (FIG. 10) and with a fluorescing disease component (FIG. 11) such that the fluorescing disease component is coated with magnetic particles.

However, it should be noted that a cluster may include many functionalized magnetic particles and does not need to include more than one disease component (FIGS. 10 and 11 are also possible; in FIG. 11, the disease component is stained with a fluorescence dye). The cell can also be coated with magnetic particles making it move into the collection region. Clusters allow for disease components to be captured and detected at smaller numbers than traditional detection schemes (i.e., the clusters amplify the detection capability for smaller numbers of disease components). Indeed, the magnetic force on the clusters due to the magnetic field gradient may be much greater than the force on an individual magnetic particle.

After placing these coated magnetic particles in a positive sample (and after waiting for a time period in which binding takes place and/or mixing the sample and magnetic particles, such as by rotation), the SARS-CoV-2 virus or associated antibodies can bind to the viral receptors/ligands or viral proteins (respectively) coating the magnetic particles. The viruses/antibodies are not themselves magnetic but become magnetic when bound to the functionalized magnetic particles coated with viral proteins or viral receptors. A magnetic particle cluster can be formed (self-assembled) when the SARS-CoV-2 virus or associated antibodies bind to the ligands/viral proteins or viral receptors coating the magnetic particles. The force on a magnetic particle cluster because of a magnetic field gradient is far greater on multiple functionalized magnetic particles than that on an individual unbound functionalized magnetic particle coated with recognition component. This increased force can be used to move, concentrate, and capture the clusters.

Additionally, a fluorescent substance (e.g., a dye or tracker) may be used to tag any disease components in the biofluid sample and/or the functionalized magnetic particles. One example fluorescent substance is a lipophilic dye. Fluorescent molecules of the fluorescent tracker may bind to the disease components in the sample (this may occur by adding the fluorescence tracker before the sample is placed in the sample holder or after the sample is placed in the sample holder at any point before the detection). Additionally, or alternatively, a different fluorescent tracker (e.g., a different color, fluoresces at a different wavelength of light, etc.) can be added to the magnetic particles. For example, the fluorescent tracker can fluoresce under the light beam and the fluorescing disease components can be detected by the imaging component (e.g., a cell phone with a fluorescence imaging attachment) using traditional fluorescence detection methods. With the imaging component, the imaging is more portable and less expensive.

It should be noted that the sample holder may have a collection region (like collection region 104 of FIG. 1) in which to collect the SARS-CoV-2 virus or antibody particles by pulling them in via one or more magnets (like magnet(s) 105 of FIG. 1). In operation, unbound functionalized magnetic particles coated with recognition component are not drawn into the collection region, while the disease component becomes bound to the functionalized magnetic particles through the recognition component and forms clusters that are drawn into the collection region. The one or more magnets can be positioned to establish a magnetic field gradient that can draw the clusters into the collection region. The magnets can be moveable or able to be shielded, in some instances, so that after the clusters are pulled into the collection region, the disease component, at least a portion of the clusters can be collected.

The magnetic particles (that are functionalized and coated with recognition component) are affected by the magnetic field gradient, but not to the same extent as clusters (e.g., single magnetic particles that are not part of a cluster also move under the magnetic field gradient, but to a lesser degree than those of the cluster). Larger magnetic particles are more affected by the magnetic field gradient than smaller magnetic particles, for example, at one magnetic field gradient strength 10 nm individual magnetic particles would not be pulled into the collection region. To keep the majority of non-clustered magnetic particles out of the collection region distinct field gradient strengths may be utilized for different size particles. The larger clusters are pulled towards the collection region at a greater speed or acceleration than the individual particles. In another example, different size magnetic particles may be used. When disease components do exist in the sample, one or more clusters are formed, and the clusters are drawn into the collection region. Any functionalized magnetic particles coated with recognition component that have not attached to a disease component are not drawn into the collection region. The magnetic field exerts a greater magnetic force on clusters that contain more than one magnetic particle than on single functionalized magnetic particles. For example, the more magnetic particles in a cluster, the greater the force of the magnetic field urging the clusters to the collection region.

The disease components can be detected (e.g., by components of imaging component 106) within the collection region (e.g., FIGS. 2-3) or as the disease components are pulled into the collection region (e.g., FIG. 4). The imaging component can include a light source and a detector (that can include a filter, a digital microscope and/or photodetector, and a computing device (e.g., a smart phone or laptop that can be attached to the digital fluorescence microscope)). The fluorescence microscope can image the collection region based on the fluorescent dye to detect the disease components. The fluorescence microscope uses light to excite the fluorescent dye and a filter to transmit light emitted by the excited fluorescent dye to the fluorescence microscope, while restricting light used to excite the fluorescent dye. The imaging component can provide the fluorescence used in magnetofluoresis. A computing device of the imaging component can determine the amount of fluorescing disease components in an image of the fluorescence qualitatively and/or quantitatively.

After the detection via magnetofluorescence (e.g., after a time period that allows for at least a majority of clusters to be pulled into the collection region), the magnetic field gradient can be removed (e.g., by moving or shielding the one or more magnets) so that the SARS-CoV-2 viruses or antibodies can be captured for further analysis. For example, when the collection region is a microfluidic channel, a PBS wash can be added to the sample holder and then withdrawn to remove nonmagnetic material and, following that, the concentrated SARS-CoV-2 viruses or antibodies can be isolated by removing the fluid (e.g., with a micropipette) and leaving only the clusters that can be captured for further analysis (either within the collection region or after transfer to another container). The analysis can be used as a patient-derived approach that allows analysis of the nuances or specificity of a potentially rapidly mutating virus or its associated antibodies in a particular patient.

References to "one aspect", "an aspect", "some aspects", "one instance", "an instance", "some instances", "one example", "an example", "some examples" and so on, indicate that the embodiment(s) or example(s) so described may include a particular feature, structure, characteristic, property, element, or limitation, but that not every embodiment or example necessarily includes that particular feature, structure, characteristic, property, element, or limitation. Furthermore, repeated use of the phrase "in an aspect" does not necessarily refer to the same embodiment, though it may.

Where the disclosure or claims recite "a," "an," "a first," or "another" element, or the equivalent thereof, it should be interpreted to include one or more than one such element, neither requiring nor excluding two or more such elements. Furthermore, what have been described above are examples. It is, of course, not possible to describe every conceivable combination of components or methods, but one of ordinary skill in the art will recognize that many further combinations and permutations are possible. Accordingly, the invention is intended to embrace all such alterations, modifications, and variations that fall within the scope of this application, including the appended claims.

What is claimed is:

1. A method comprising:
combining a sample with a fluorescent dye and a plurality of magnetic particles in a device;
tagging disease components in the sample with the fluorescent dye and the plurality of magnetic particles;
using at least one magnet to provide a magnetic field that draws the tagged disease components from the device into a collection region, wherein the collection region is a small portion of the device located at a side of the device in an original orientation of the device;

removing non-magnetic portions of the sample from the sample while holding the tagged disease components with the magnetic particles in the collection region by the magnetic field of the magnet;
rotating the device and the at least one magnet ninety degrees so that the collection region is at a bottom of the device
removing the at least one magnet after the device is rotated, wherein the magnetic material is held in the collection region by gravity;
replacing the magnet with a fluorescence microscope; and
imaging the collection region with the fluorescence microscope using the fluorescent dye to detect the tagged disease components, wherein the fluorescence microscope uses light to excite the fluorescent dye and a filter to transmit light emitted by the fluorescent dye to the fluorescence microscope, while restricting light used to excite the fluorescent dye.

2. The method of claim 1, wherein the fluorescence microscope sends a signal to a smartphone, a tablet, or a laptop computer to detect fluorescing disease components.

3. The method of claim 2, further comprising providing an image of the detected fluorescing disease components.

4. The method of claim 3, further comprising providing a count of a number of the detected fluorescing disease components translated per volume of sample tested.

5. The method of claim 4, wherein the volume of sample tested is between 1 mL and 10 mL.

6. The method of claim 1, further comprising setting a field of view for the fluorescence microscope to be a same size as the collection region.

7. The method of claim 1, wherein the device is a cuvette.

8. The method of claim 7, further comprising using a micropipette to remove fluid from the cuvette, leaving the tagged disease component in the collection region.

9. The method of claim 8, further comprising removing nonmagnetic material from the collection region by rinsing the device with a buffer.

10. The method of claim 1, wherein the detecting further comprises using a photodiode to detect an intensity of light emitted by the fluorescent dye.

11. A system comprising:
a device with a collection region, wherein the device is configured to hold a sample that is combined with a fluorescent dye and a plurality of magnetic particles such that disease components in the sample are tagged with the fluorescent dye and the plurality of magnetic particles, wherein the device is configured to be rotated such that the collection region is at a bottom of the device after the sample is combined with the fluorescent dye and the plurality of magnetic particles;
at least one magnet, removeably positioned near the collection region, configured to establish a magnetic field gradient to draw the tagged disease components into the collection region of the device when the magnet is positioned near the collection region, wherein the magnet is configured to hold the tagged disease component in the collection region while non-magnetic parts of the sample are removed from the device, and wherein the magnet is configured to be removed from near the collection region when the non-magnetic parts of the sample have been removed; and
a fluorescence microscope configured to be positioned near the collection region in place of the at least one magnet, when the magnet has been removed, and to image the collection region using the fluorescent dye to detect the tagged disease components, wherein the fluorescence microscope uses light to excite the fluorescent dye and a filter to transmit light emitted by the fluorescent dye to the fluorescence microscope, while restricting light used to excite the fluorescent dye.

12. The system of claim 11, wherein the fluorescence microscope located beneath the collection region to detect the disease components based on the fluorescent dye.

13. The system of claim 11, wherein the fluorescence microscope sends a signal to a computer, a smartphone, a tablet, or a laptop computer to detect fluorescing disease components.

14. The system of claim 11, wherein a field of view for the fluorescence microscope is a same size as the collection region.

15. The system of claim 11, wherein the device is a cuvette.

16. The system of claim 11, further comprising a photodiode to detect an intensity of light emitted by the fluorescent dye.

17. The system of claim 16, wherein the fluorescence microscope comprises the photodiode.

18. The system of claim 11, wherein a micropipette is used to remove fluid from the device, leaving the tagged disease component in the collection region.

19. The system of claim 11, further comprising a mirror device positioned to redirect light from fluorescing disease components to the fluorescence microscope.

*  *  *  *  *